United States Patent [19]

DeBoer

[11] Patent Number: 4,551,433

[45] Date of Patent: Nov. 5, 1985

[54] MICROBIAL HYBRID PROMOTERS

[75] Inventor: Herman A. DeBoer, Pacifica, Calif.

[73] Assignee: Genentech, Inc., San Francisco, Calif.

[21] Appl. No.: 338,397

[22] Filed: Jan. 11, 1982

Related U.S. Application Data

[63] Continuation-in-part of Ser. No. 264,306, May 18, 1981, abandoned, and a continuation-in-part of Ser. No. 328,174, Dec. 7, 1981, abandoned.

[51] Int. Cl.$^4$ .................. C12N 1/20; C12N 15/00; C12N 1/00; C12P 21/00; C12P 21/02; C12P 21/04; C07H 21/04; C12R 1/19
[52] U.S. Cl. ............................... 435/253; 435/68; 435/70; 435/71; 435/172.3; 435/317; 435/849; 536/27; 935/38; 935/41; 935/61; 935/73
[58] Field of Search .................. 35/68, 70, 172, 253, 35/317, 849, 172.3, 71; 536/27

[56] References Cited

PUBLICATIONS

Heynecker et al.: Nature 263, 748 (1976).
DeBoer et al.: In Promoters, Structure and Function, Rodriguez et al. (ed.), Praeger Scientific (1982), pp. 462–481.
Nagahari: J. Bacteriol. 136, 312, (1978).
Ihara et al.: Biochim., Biophys. Acta 432, 199 (1976).
DeBoer et al.: J. Biol. Chem. 254, 5609 (1979).
DeBoer et al.: Cell 17, 201 (1979).
Young et al.: Cell 17, 225 (1979).
Siebenlist et al.: Cell 20, 269 (1980).
Rosenberg et al.: Ann. Rev. Genet. 13, 319 (1979).
Hamming et al.: Nucl. Acids Res. 7, 1019 (1979).

*Primary Examiner*—Thomas G. Wiseman
*Assistant Examiner*—James Martinell

[57] ABSTRACT

Novel microbial hybrid promoters and their use to direct the microbial expression of heterologous genes are described. Such promoters are selectively and functionally constructed by recombinant techniques, utilizing the discovery that certain DNA regions of given promoters are responsible for particularly advantageous functional properties.

15 Claims, 8 Drawing Figures

Fig. 6
Start

Fig.6
Conclusion

Fig. 7

```
PlacUV5      CACCCCAGGCTTTACACTTTATGCTTCCGGCTCGTATAATGTGTGGAATTG
             GTGGGTCCGAAATGTGAAATACGAAGGCCGAGCATATTACACACCTTAAC
                              -35              HpaII        +1

PrrnB        EcoRI    (106 bp)  AAATTTCCTCTTGTCAGGCCGGAATAACTCCCTATAATGCGCCACCACTGA
                                TTTAAAGGAGAACAGTCCGGCCTTATTGAGGGATATTACGCGGTGGTGACT
                                               -35              HpaII        +1

Prrn-lac I            AAATTTCCTCTTGTCAGGCCGGCTCGTATAATGTGTGGAATTG
                      TTTAAAGGAGAACAGTCCGGCCGAGCATATTACACACCTTAAC
                                 -35              HpaII    +1
                      21 bp synthetic DNA inserted at HpaII site SacI XhoI       XbaI Prrn-lac II  AAATTTCCTCTTGTCAGGCCGGAGCTCGAGTCTAGAATCGGCTCGTATAATGTGTGGAATTG
             TTTAAAGGAGAACAGTCCGGCCTCGAGCTCAGATCTTAGCCGAGCATATTACACACCTTAAC
                      SacI XbaI - S1                                    +1
                           deleted
                                 -35

Prac 5-16    EcoRI    (106 bp)  AAATTTCCTCTTGTCAGGCCGGAATCGGCTCGTATAATGTGTGGAATTG (lac operator)(HGH gene)
                                TTTAAAGGAGAACAGTCCGGCCTTAGCCGAGCATATTACACACCTTAAC                EcoRI
                                               -35                           +1
                                Prrn-sequences       Plac sequences
```

Fig. 8

MICROBIAL HYBRID PROMOTERS

CROSS-REFERENCE TO RELATED APPLICATION

This is a continuation-in-part of applications U.S. Ser. No. 264,306, now abandoned, filed May 18, 1981 and U.S. Ser. No. 328,174, now abandoned, filed Dec. 7, 1981.

FIELD OF THE INVENTION

The present invention relates to novel microbial promoter/operator systems which direct the efficient and controlled production of polypeptides by microbial expression of heterologous genes. The present novel microbial promoter/operators are hybrids of promoters which functionally interact with *E. coli* DNA-dependent RNA polymerase. They are constructed according to known methods of recombinant DNA technology, utilizing the discovery that certain regions of the DNA sequences of various known promoter systems are responsible for their characteristic advantages under given conditions. These regions are isolated and selectively and functionally rejoined in such a way that novel hybrid promoter/operators are provided which exhibit overall new advantageous properties. Thus, the present invention permits the construction of novel hybrid promoter/operators which are highly specific, tailored to achieve optimal efficiency and control in the regulation of microbial expression of heterologous genes.

BACKGROUND OF THE INVENTION

With the advent of recombinant DNA technology, the controlled microbial production of an enormous variety of useful polypeptides has become possible. Many mammalian polypeptides, such as leukocyte interferons, have already been produced by various microorganism strains. The power of the technology admits the microbial production of an enormous variety of useful polypeptides, putting within reach the microbially directed manufacture of hormones, enzymes, antibodies, and vaccines useful against a wide variety of diseases.

A basic element of recombinant DNA technology is the plasmid, a nonchromosomal loop of double-stranded DNA found in bacteria oftentimes in multiple copies per cell. Included in the information encoded in the plasmid DNA is that required to reproduce the plasmid in daughter cells (i.e., a "replicon") and ordinarily, one or more selection characteristics, such as resistance to antibiotics, which permit clones of the host cell containing the plasmid of interest to be recognized and preferentially grown in selective media. The utility of bacterial plasmids lies in the fact that they can be specifically cleaved by one or another restriction endonuclease or "restriction enzyme", each of which recognizes a different site on the plasmidic DNA. Thereafter heterologous genes or gene fragments may be inserted into the plasmid by endwise joining at the cleavage site or at reconstructed ends adjacent the cleavage site. (As used herein, the term "heterologous" refers to a gene not ordinarily found in, or a polypeptide sequence ordinarily not produced by, a given microorganism, whereas the term "homologous" refers to a gene or polypeptide which is found in, or produced by the corresponding wild-type microorganism.) DNA recombination is performed outside the microorganism, and the resulting "recombinant" replicable expression vehicle, or plasmid, can be introduced into microorganisms by a process known as transformation and large quantities of the heterologous gene-containing recombinant vehicle obtained by growing the transformant. Moreover, where the gene is properly inserted with reference to portions of the plasmid which govern the transcription and translation of the encoded DNA message, the resulting expression vehicle can be used to actually produce the polypeptide sequence for which the inserted gene codes, a process referred to as expression. Expression is initiated in a region known as the promoter. RNA polymerase recognizes a promter and binds to it prior to initiation of transcription. In some cases, as in the lac and trp systems discussed infra, promoter regions are overlapped by "operator" regions to form a combined promoter-operator. Operators are DNA sequences which are recognized by so-called repressor proteins which serve to regulate the frequency of transcription initiation in a particular promoter. In the transcription phase of expression, the RNA polymerase recognizes certain sequences in and binds to the promoter DNA. The binding interaction causes an unwinding of the DNA in this region, exposing the sense coding strand of the DNA as a template for initiated synthesis of messenger RNA from the 5' to 3' end of the entire DNA sequence. The messenger RNA is, in turn, bound by ribosomes within which the encoded message is translated into a polypeptide having the amino acid sequence for which the DNA codes. Each amino acid is encoded by a unique nucleotide triplet or "codon" which collectively make up the "structural gene", i.e., that part which encodes the amino acid sequence of the expressed polypeptide product.

After binding to the promoter, the RNA polymerase initiates first the transcription of nucleotides encoding a ribosome binding site including a translation initiation or "start" signal (ordinarily ATG, which in the resulting messenger RNA becomes AUG), then the nucleotide codons within the structural gene itself. So-called stop codons are transcribed at the end of the structural gene whereafter the polymerase may form an additional sequence of messenger RNA which, because of the presence of the stop signal, will remain untranslated by the ribosomes.

Ribosomes bind to the binding site provided on the messenger RNA, in bacteria ordinarily as the mRNA is being formed, and themselves direct the production of the encoded polypeptide, beginning at the translation start signal and ending at the previously mentioned stop signal(s). The desired polypeptide product is produced if all remaining codons follow the initiator codon in phase. The resulting product may be obtained by lysing the host cell and recovering the product by appropriate purification from other bacterial protein.

Polypeptides expressed through the use of recombinant DNA technology may be entirely heterologous, as in the case of the direct expression of human growth hormone, or alternatively may comprise a heterologous polypeptide and, fused thereto, at least a portion of the amino acid sequence of a homologous polypeptide, as in the case of the production of intermediates for somatostatin and the components of human insulin. In the latter cases, for example, the fused homologous polypeptide comprised a portion of the amino acid sequence for beta galactosidase. In those cases, the intended bioactive product is bioinactivated by the fused, homologous polypeptide until the latter is cleaved away in an extracellular environment. Fusion proteins like those just mentioned can be designed so as to permit highly specific cleavage of the precusor protein from the intended product, as by the action of cyanogen bromide on methionine, or alternatively by enzymatic cleavage. See, e.g., G.B. Patent Publication No. 2 007 676 A.

If recombinant DNA technology is to fully sustain its promise, systems must be devised which optimize expression of gene inserts, so that the intended polypeptide products can be made available in controlled environments and in high yields.

The lactose promoter/operator systems have been commonly employed but, while useful, do not fully utilize the capacity of the technology from the standpoint of yield. However, they have the distinct advantage of being very controllable, a characteristic which is very desirable where large-scale microbial fermentation production is concerned. The control mechanism lies in the mode of action of the operator. When the operator is in a repressed mode, because of bound repressor protein, the DNA dependent RNA polymerase is competitively prevented from binding and initiating transcription. Thus, the transcriptional pathway is closed, and this effectively blocks promoter operability. This system can be derepressed by induction following the addition of a known inducer, such as isopropyl-beta-D-galactoside. (IPTG). The inducer causes the repressor protein to fall away so the RNA polymerase can function. Thus, these types of promoter/operators are said to be "inducible." Cells transformed with plasmids carrying the so-called lac promoter/operator system can be permitted to grow up to maximum density while maintaining the promoter/operator system in a repressed state simply by omission of an inducer, such as IPTG, in the fermentation culture. When a high level of cell density is achieved, the system can be derepressed by additon of inducer and the promoter is then free to initiate transcription so as to obtain optimal expression of the gene products at yields commensurate with the promoter strength. However, despite these advantages, certain of the inducible promoters, such as the lac promoter/operator system are relatively weak and productions utilizing such promoters do not urge the microorganism to generate maximum output.

As a response to the need for microbial expression vehicles capable of producing desired polypeptide products in higher yield, the so-called tryptophan promoter/operator was harnessed and is currently widely used. The tryptophan promoter/operator system is one of many known, relatively powerful systems—upwards of three to four times the strength of the lac promoter. Although the power of such systems is attractive for commercial production, the advantages of this power are somewhat offset by less promoter control. In many of these powerful systems, the operator is not inducible in the sense defined above. Instead, the bound repressor which closes down the promoter pathway is not removable by induction. Another system was devised whereby the attenuator region of the tryptophan promoter/operator system was removed and the cells transformed with this system grown up in the presence of tryptophan rich media. This provided sufficient tryptophan to essentially completely repress the operator so that cell growth could proceed uninhibited by premature expression of the desired heterologous polypeptide system. When the culture reached appropriate growth levels, no additional tryptophan was supplied, resulting in mild tryptophan limitation and, accordingly, derepression of the promoter with highly efficient expression of the heterologous insert. However ingenious, this system, on an industrial scale, does not have the refined control characteristics of a promoter system having an operator which can be completely repressed and derepressed by induction. In practice, for example, it is necessary to maintain high levels of tryptophan during the growing up phase to completely repress the promoter and to permit the medium to become exhausted of tryptophan following full growth of the culture. It is apparent, therefore, that a need has existed for a microbial promoter/operator system which is capable of highly controlled production of desired polypeptide products in high yield.

The present invention addresses the problems associated with present promoter/operator systems and uniquely provides new hybrid systems which exhibit substantial advantages. The present invention is further directed to a method of microbially producing heterologous polypeptides, directed by highly efficient and controlled promoter/operator systems, as well as associated means. It is particularly directed to the use of hybrid promoter/operator systems which are designed to function well in large, industrial scale production.

SUMMARY OF THE INVENTION

According to the present invention, novel hybrid promoter/operator systems are provided for use in replicable expression vehicles designed to direct the production of heterologous polypeptide in a transformant microorganism. In these replicable expression vehicles, the novel hybrid promoter/operator systems of this invention are operably linked to a heterologous gene insert encoding a heterologous polypeptide which is not normally produced by the transformed microorganism when in its natural untransformed state. The present invention is further directed to the novel replicable expression vehicles containing the novel hybrid promoter/operator systems hereof, as well as microorganisms transformed with said vehicles. The present invention is further directed to methods and means for the direction of controlled, high level production of heterologous polypeptides in microorganisms employing such novel hybrid promoter/operator systems and to specific embodiments thereof.

Using conventional numbering, the first area of main sequence homology within given promoter/operators occurs at about the −10 nucleotide base of the DNA sequence. This is the region of the so-called Pribnow box consensus sequence, its prototypic sequence being TATAATG in which the last T—namely thymine—is identical in all promoters which have been investigated. A second region of homology centers around position −35 of the DNA sequence. This so-called −35 consensus sequence has a highly conserved trinucleotide TTG sequence, followed by a less stringently conserved sequence of a total hexomer—TTGACA—which is part of a stretch of twelve nucleotides in which additional homologies can be found. It is these two areas of homology that the *E. coli* RNA polymerase is believed to recognize and functionally bind most tightly. The major contact between the RNA polymerase enzyme and the promoter DNA creates "open" regions which are believed to facilitate a proper recognizition of the site where messenger RNA formation by transcription is to be initiated. This transcription initiation site, by convention, is labelled as +1 on the DNA sequence. Again, the region between the Pribnow box and the −35 consensus sequences, ranging from about 15 to about 25 nucleotide bases in length, does not appear to have significant regions of homology from one promoter to another. Thus, this region is not believed to be significant for functional binding of the RNA polymerase. (See Hermann Bujard, *Trends in Biological Sciences,* October 1980, page 274, and Siebenlist, U. et al. *Cell* 20, 269 (1980), each of which is incorporated herein by reference.) This invention demonstrates that this region also may not be significant, as far as sequence is concerned, with respect to signal strength and operator function.

The novel hybrid promoter/operator systems of the present invention are capable of directing *E. coli* DNA-dependent RNA polymerase transcription and comprise a promoter/operator sequence capable of being derepressed by induction and exhibiting a first signal strength, and, operably positioned upstream therefrom; a fragment comprising the $-35$ consensus sequence and 5' flanking region of a second promoter having a greater signal strength; said sequences covalently linked between about said $-35$ consensus sequence and the Pribnow box of said promoter/operator sequence.

Thus, a first *E. coli* DNA-dependent RNA polymerase interacting promoter having an operator which is capable of being derepressed by induction is cleaved at a point lying between about its Pribnow box and $-35$ consensus sequences. A second *E. coli* DNA-dependent RNA polymerase interacting promoter having a greater signal strength than the first is similarly cleaved. In preferred embodiments, the regions of cleavage lie between about nucleotide base pairs $-10$ and $-35$. The cleaved DNA sequences are then ligated according to known methods.

Preferably, the restriction sites are selected so as to produce complementary ends which admit of ready endwise ligation. Alternatively, linkage can be effected after introduction of complementary restriction sites on the two sequences by reconstruction of the ends adjacent the cleavage sites, preferably using synthetically derived linker nucleotides. In one embodiment, the two DNA sequences, having non-complementary restriction sites, can be ligated to a synthetic insert specifically prepared to match the respective restriction sites of the two DNA sequences. This insert in turn can also contain different, unique restriction sites which permit excision of portions when it is desired to obtain promoters having varied distances between the Pribnow box and $-35$ consensus sequences.

In the preferred embodiments, restriction sites are chosen or constructed such that the resultant hybrid promoter/operator will have a DNA region between its Pribnow box and $-35$ consensus sequences which is approximately the same length as the corresponding regions in the parent promoters.

The hybrid promoter/operator systems of the present invention contain a sequence of double stranded DNA comprising, in order, nucleotide bases corresponding to an inducible operator, transcription initiation site and Pribnow box consensus sequence linked, via a sequence of nucleotides formed by DNA recombination, to a sequence of nucleotide bases of a $-35$ consensus sequence and 5' flanking region thereof. The bases of the operator and initiation site are derived from, or patterned after, a promoter/operator having an inducible operator, as defined herein, and the bases of the $-35$ consensus sequence et seq. are derived from, or patterned after, a promoter having a greater signal strength than said promoter/operator. The linker sequence formed by DNA recombination is derived either by complementary ligation of the cleaved sequences from the parent promoters or is synthetically produced, optionally along with the corresponding downstream and upstream DNA sequences, as described above. In any event, where reconstruction is employed to produce complementary ends, the Pribnow box and/or $-35$ consensus sequences are preferably repaired so as to optimally restore the original homology.

In one aspect, the present invention provides nucleotide sequences downstream from about the Pribnow Box sequence that are patterned after sequences corresponding to those of a promoter/operator having an inducible operator. Thus, synthetically derived DNA can be employed to provide one or another fragment in making up the hybrid promoters hereof. For example, synthetic or natural sequences of the $-35$ consensus sequence of one promoter can be appropriately joined in accordance herewith, for example at about the Pribnow Box region, with synthetic or natural sequences of a given, second, inducible promoter or with synthetic DNA fragment(s) comprising an operator, Shine-Dalgarno sequence and transcription initiation site corresponding to a given, second, inducible promoter. Again, the DNA fragment may also contain various, unique restriction sites facilitating its ligation with the $-35$ sequence fragment and the translational start codon and heterologous gene sequence positioned downstream therefrom. Further, such DNA fragment may also contain unique restriction sites surrounding the Shine-Dalgarno sequence enabling its portability and hence exchangability.

The novel hybrid promoter/operators of the present invention, when employed within replicable expression vehicles, are operably linked to nucleotides encoding the translation initation and structural gene encoding the amino acid sequence of the desired heterologous polypeptide.

Promoters which have an operator which is capable of derepression by induction include: lac, lambda PR, lambda PL, gal P2, era BAD, ara C, tet, str, spc, rpoB, L11, and gal P1. See Siebenlist, U., et/al., Supra. Promoters which display relatively high signal strengths include: trp, rrn family, tRNA family, $T_7A_3$, $T_7A_1$, lambda PR, lambda PL, str, spc, tufA, rpoB, and tufB. See Siebenlist, U., et/al. Supra.

Factors which are believed to contribute to relative strength of promoters include composition and sequence integrity of Pribnow box and $-35$ consensus sequences, the distance between Pribnow box and $-35$ consensus sequences and the composition of the 5' flanking region upstream from the $-35$ consensus sequence, notably in the region in and about the $-40$ nucleotide base. With strong promoters, this region of the DNA sequence contains extremely A/T-rich regions with clusters of A/T and T/A base pairs. This invention shows that a signal, significant region responsible for high strength of a given promoter is that region upstream from the $-35$ promoter consensus sequence. This invention also demonstrates that promoters of the first category, being inducible in derepression, are not influenced particularly in this characteristic by the DNA makeup upstream from about the Pribnow box consensus sequence.

The region between the Pribnow box and $-35$ consensus sequences may contain naturally occuring restriction endonuclease cleavage sites. In the preparation of the novel hybrid promoter/operators of the present invention, advantage is taken of such sites to form fragments which can be ligated with corresponding fragments from other promoters. Thus, for example, where a common restriction endonuclease cleavage site exists in two suitable donor promoters, cleavage and subsequent appropriate ligation is easily achieved while maintaining functional inphase sequencing. If endonuclease cleavage sites exist which are not identical, advantage can be taken of the known patterns of cleavage and subsequent ligation. This is generally within the skill of the artisan.

The preferred embodiments of the invention involve use of a number of commonly available restriction endonucleases next identified, by way of example only, with their corresponding recognition sequences and (indicated by arrow) cleavage patterns.

| XbaI: | ↓<br>TCTAGA<br>AGATCT<br>↑ | TaqI: | ↓<br>TCGA<br>AGCT<br>↑ |
|---|---|---|---|
| EcoRI: | ↓<br>GAATTC<br>CTTAAG<br>↑ | HindIII: | ↓<br>AAGCTT<br>TTCGAA<br>↑ |
| BglII: | ↓<br>AGATCT<br>TCTAGA<br>↑ | HpaI: | ↓<br>GTTAAC<br>CAATTG<br>↑ |
| PvuII: | ↓<br>GAGCTG<br>GTCGAC<br>↑ | PstI: | ↓<br>CTGCAG<br>GACGTC<br>↑ |
| BamHI: | ↓<br>GGATCC<br>CCTAGG<br>↑ | | |

Where the points of cleavage are spaced apart on the respective strands the cleaved ends will be "sticky", i.e., capable of reannealing or of annealing other complementarily "sticky"-ended DNA by Watson-Crick base pairing (A to T and G to C) in mortise and tenon fashion. Some restriction enzymes, such as HpaI and PvuII above, cleave to leave "blunt" ends. The nucleotide sequences above are represented in accordance with the convention used throughout: upper strand is the protein encoding strand, and in proceeding from left to right on that strand one moves from the 5' to the 3' end thereof, i.e., in the direction of trancription from a "proximal" toward a "distal" point.

In the event that the particular promoter/operator starting materials do not contain any, or any advantageous, restriction endonuclease cleavage sites, the double stranded DNA may, by a method which is useful for cleavage, be treated at any specifically desired site. In this method, the double stranded DNA is converted to single stranded DNA in the region surrounding the intended cleavage point, such as by reaction with exonuclease. A synthetic or other single-stranded DNA primer is then hybridized to the single stranded length earlier formed, by Watson-Crick base pairing, the primer being such as to ensure that the 5' and thereof will be coterminus with the nucleotide on the first strand just prior to the intended cleavage point. The primer is next extended in the 3' prime direction by reaction with DNA polymerase, recreating that portion of the original doublestranded DNA prior to the intended cleavage that was lost in the first step. Simultaneously or thereafter, the portion of the first strand beyond the intended cleavage point is digested away. In the most preferred embodiment, the extension from primer and single strand digestion steps are performed simultaneously, using a polymerase that simultaneous digests the protruding single stranded end in the 3' to 5' direction and extends the primer in the 5' to 3' direction. The preferred material for this purpose is Klenow Polymerase I, i.e., that fragment obtained by proteolytic cleavage of DNA polymerase I which contains the 5' to 3' polymerizing activity and the 3' to 5' exonucleolytic activity of the parental enzyme, yet lacks its 5' to 3' exonucleolytic activity. See A. Kornberg, *DNA Synthesis,* 98, W. H. Freeman and Company, San Francisco (1974).

The ligation of the formed fragments upon such cleavage or by cleavage at a restriction endonuclease cleavage site, may be effected, e.g., by blunt end ligation or other methods which are apparent to the skilled artisan.

Microorganisms transformed, via known methods, with replicable expression vehicles containing the novel hybrid promoter/operator systems hereof can grow up to levels appropriate for industrial production of the polypeptide, with the promoter/operator in a repressed state. After substantially full growth is achieved, an inducer is supplied from an external source and, accordingly, the operator is derepressed and highly efficient expression of the heterologous insert occurs. In this manner, the cells are never prematurely killed in the event that the heterologous polypeptide produced is lethal to the cell and furthermore, the cell culture provides maximal production of the heterologous polypeptide inasmuch as it is at or near its maximum growth state. Thus provided, is a highly controlled and efficient expression vehicle which is particularly useful for the production of the high levels of heterologous polypeptides demanded by present day highly refined recombinant DNA technology.

All microorganism strains used in the hybrid promoter/operator system directed expression, according to this invention, are *E. coli* strains which utilize the *E. coli* DNA-dependent RNA polymerase (Enzyme No. E.C. 2.7.7.6). The invention, in its most preferred embodiment, is described with reference to *E. coli* strain D 1210, but it is understood that other known *E. coli* species such as *E. coli* B, *E. coli* K-12 and other *E. coli* strains may be employed, for example, *E. coli* K-12 294 (ATCC Accession No.31446), *E. coli* K-12 RR1 (ATCC Accession No. 31343) *E. coli* K-12 X1776 (ATCC Accession No. 31537), and *E. coli* RV308 (ATCC Accession No. 31608). Many of these are deposited and (potentially) available from recognized microorganism depository institutions, such as the American Type Culture Collection (ATCC)-cf. the ATCC catalogue listing. See also German Offenlegungsschrift No. 2644432. As mentioned, particularly preferred is *E. coli* strain D 1210 having the following morphological characteristics: lac+, iq, o+, z+, y+, thi−, leu−, pro−gal−, str$^r$, B$_1^-$, recA−, r−, m$_B^-$. A sample of this microorganism harboring an insulin B-gene has been deposited (ATCC Accession No. 31449).

BRIEF DESCRIPTION OF THE DRAWINGS

FIG. 3 depicts the DNA sequences of the trp promoter, the lac UV5 promoter and two tac hybrid promoter/operators whose construction is illustrated by FIG. 2 and is described in more detail infra. The DNA sequences of the trp- and lac-promoters are known—cf. Siebenlist et al. Supra. The DNA sequences of the tac-promoters were determined using the dideoxy sequencing method using denatured plasmid DNA to which a synthetic single stranded DNA fragment matching the −40 area of the trp-promoter was annealed. The Shine-Dalgarno and the start-codon of the HGH gene are overlined. The Pribnow boxes and −35 sequences of the promoters are underlined. The operator sequences are indicated with broken lines. The starting nucleotides are indicated with +1. The relevant restriction sites TaqI and HpaII are indicated by arrows. In the case of the tac-promoters, the junctions between the "trp" and "lac" sequences are indicated with double arrows. The nucleotide distance between the −35 consensus sequence and Pribnow box is 17 bp for Ptrp, 18 bp for Ptac, 16 bp for Ptac I and 17 bp for Ptac II.

FIG. 4 is an illustration of human growth hormone (HGH) production promoted by the hybrid promoter/operator whose construction is illustrated by FIG. 2. Fresh overnight cultures of E. coli D1210/pHGH807-tacI and E. coli D1210/pHGH 107-11 (prepared by standard transformation procedures) were used to inoculate 50 ml LB-ampicillin (20 ug/ml) to a cell-density of 0.03 ($OD_{550}$). After one hour the first sample was taken (t=0 min). Induction of the tac-promoter in $D_{1210}$ was done by addition of 1.0 mM IPTG at t=80 min. (shown by arrow). HGH levels were determined in a radioimmunoassay. Symbols: ●-● : $D_{1210}$/pHGH107-11 (single lac-promoter); ■-■ : $D_{1210}$/pHGH807- tacI (single tac-promoter). Production of HGH using the pHGH907tacII hybrid promoter/operator hereof is substantially identical to the levels obtained using the pHGH807tacI promoter/operator, as shown in this figure. Likewise, production of HGH using the Prrnlac hybrid promoter/operator hereof is similar to the levels obtained using the Ptac promoter/operator, as shown in FIG. 4 (data not shown).

DETAILED DESCRIPTION

1. Construction of pHGH 207-1

Plasmid pGM1 carries the E. coli tryptophan operon containing the deletion LE1413 (G. F. Miozzari, et al., (1978) J. Bacteriology 1457–1466)) and hence expresses a fusion protein comprising the first 6 amino acids of the trp leader and approximately the last third of the trp E polypeptide (hereinafter referred to in conjunction as LE′), as well as the trp D polypeptide in its entirety, all under the control of the trp promoter-operator system. The plasmid, 20 ug, was digested with the restriction enzyme PvuII which cleaves the plasmid at five sites. The gene fragments were next combined with EcoRI linkers (consisting of a self complementary oligonucleotide of the sequence: pCATGAATTCATG) providing an EcoRI cleavage site for a later cloning into a plasmid containing an EcoRI site. The 20 ug of DNA fragments obtained from pGM1 were treated with 10 units $T_4$ DNA ligase in the presence of 200 pico moles of the 5′-phosphorylated synthetic oligonucleotide pCATGAATTCATG and in 20ul $T_4$ DNA ligase buffer (20mM tris, pH 7.6, 0.5 mM ATP, 10 mM $MgCl_2$, 5 mM dithiothreitol) at 4° C. overnight. The solution was then heated 10 minutes at 70° C. to inactivate ligase. The linkers were cleaved by EcoRI digestion and the fragments, now with EcoRI ends were separated using polyacrylamide gel electrophoresis (hereinafter "PAGE") and the three largest fragments isolated from the gel by first staining with ethidium bromide, locating the fragments with ultraviolet light, and cutting from the gel the portions of interest. Each gel fragment, with 300 microliters 0.1xTBE, was placed in a dialysis bag and subjected to electrophoresis at 100 V for one hour in 0.1xTBE buffer (TBE buffer contains: 10.8 gm tris base, 5.5 gm boric acid, 0.09 gm $Na_2EDTA$ in 1 liter $H_2O$). The aqueous solution was collected from the dialysis bag, phenol extracted, chloroform extracted and made 0.2 M sodium chloride, and the DNA recovered in water after ethanol precipitation. (All DNA fragment isolations hereinafter described are performed using PAGE followed by the electroelution method just discussed.) The trp promoter-operator-containing gene with EcoRI sticky ends was identified in the procedure next described, which entails the insertion of fragments into a tetracycline sensitive plasmid which, upon promoter-operator insertion, becomes tetracycline resistant.

Plasmid pBRH1, (R. I. Rodriguez, et al., Nucleic Acids Research 6, 3267–3287 [1979]) expresses ampicilin resistance and contains the gene for tetracycline resistance but, there being no associated promoter, does not express that resistance. The plasmid is accordingly tetracycline sensitive. By introducing a promoter-oper- ator system in the EcoRI site, the plasmid can be made tetracycline resistant.

pBRH1 was digested with EcoRI and the enzyme removed by phenol/CHCl3 extraction followed by chloroform extraction and recovered in water after ethanol precipitation. The resulting DNA molecule was, in separate reaction mixtures, combined with each of the three DNA fragments obtained as decribed above and ligated with T4 DNA ligase as previously described. The DNA present in the reaction mixture was used to transform competent E. coli K-12 strain 294 (K. Backman et al., Proc Nat'l Acad Sci USA 73, 4174–4198 (1976) (ATCC no. 31446) by standard techniques (V. Hershfield et al., Proc Nat'l Acad Sci USA 71, 3455-3459 (1974) and the bacteria plated on LB plates containing 20 ug/ml ampicillin and 5 ug/ml tetracycline. Several tetracycline-resistant colonies were selected, plasmid DNA isolated and the presence of the desired fragment confirmed by restriction enzyme analysis. The resulting plasmid, designated pBRHtrp, expresses β-lactamase, imparting ampicillin resistance, and it contains a DNA fragment including the trp promoter-operator and encoding a first protein comprising a fusion of the first six amino acids of the trp leader and approximately the last third of the trp E polypeptide (this polypeptide is designated LE'), and a second protein corresponding to approximately the first half of the trp D polypeptide (this polypeptide is designated D'), and a third protein coded for by the tetracycline resistance gene.

pBRH trp was digested with EcoRI restriction enzyme and the resulting fragment 1 isolated by PAGE and electroelution. EcoRI-digested plasmid pSom 11 (K. Itakura et al, Science 198, 1056 (1977); G.B. patent publication No. 2 007 676 A) was combined with this fragment 1. The mixture was ligated with T4 DNA ligase as previously described and the resulting DNA transformed into E. coli K-12 strain 294 as previously described. Transformant bacteria were selected on ampicillin-containing plates. Resulting ampicillin-resistant colonies were screened by colony hybridization (M. Gruenstein et al., Proc Nat'l Acad Sci USA 72, 3951–3965 [1975]) using as a probe the trp promoter-operator-containing fragment 1 isolated from pBRHtrp, which had been radioactively labelled with P32. Several colonies shown positive by colony hybridization were selected, plasmid DNA was isolated and the orientation of the inserted fragments determined by restriction analysis employing restriction enzymes BglII and BamHI in double digestion. E. coli 294 containing the plasmid designated pSOM7 2, which has the trp promoter-operator fragment in the desired orientation was grown in LB medium containing 10 ug/ml ampicillin. The cells were grown to optical density 1 (at 550 nM), collected by centrifugation and resuspended in M9 media in tenfold dilution. Cells were grown for 2-3 hours, again to optical density 1, then lysed and total cellular protein analyzed by SDS (sodium dodcyl sulfate) area (15 percent) polyacrylamide gel electrophoresis (J. V. Maizel Jr. et al., Meth Viral 5, 180-246 (1971)).

The plasmid pSom7Δ2, 10 μg, was cleaved with EcoRI and the DNA fragment 1 containing the tryptophan genetic elements was isolated by PAGE and electroelution. This fragment, 2 μg, was digested with the restriction endonuclease Taq I, 2 units, 10 minutes at 37° C. such that, on the average, only one of the approximately five Taq I sites in each molecule is cleaved. This partially digested mixture of fragments was separated by PAGE and an approximately 300 base pair fragment 2 that contained one EcoRI end and one Taq I end was isolated by electroelution. The corresponding Taq I site is located between the transcription start and translation start sites and is 5 nucleotides upstream from the ATG codon of the trp leader peptide. By proceeding as described, a fragment could be isolated containing all control elements of the trp operon, i.e., promoter-operator system, transcription initiation signal, and part of the trp leader ribosome binding site.

The Taq I residue at the 3' end of the resulting fragment adjacent the translation start signal for the trp leader sequence was next converted into an XbaI site. This was done by ligating the Fragment 2 obtained above to a plasmid containing a unique (i.e., only one) EcoRI site and a unique XbaI site. For this purpose, one may employ essentially any plasmid containing, in order, a replicon, a selectable marker such as antibiotic resistance, and EcoRI, XbaI and BamHI sites. Thus, for example, an XbaI site can be introduced between the EcoRI and BamHI sites of pBR322 (F. Bolivar et al., Gene 2, 95–119 [1977]) by, e.g., cleaving at the plasmid's unique HindIII site with HindIII followed by single strand-specific nuclease digestion of the resulting sticky ends, and blunt end ligation of a self annealing double-stranded synthetic nucleotide containing the recognition site such as CCTCTAGAGG. Alternatively, naturally derived DNA fragments may be employed, as was done in the present case, that contain a single XbaI site between EcoRI and BamHI cleavage residues. Thus, an EcoRI and BamHI digestion product of the viral genome of hepatitis B was obtained by conventional means and cloned into the EcoRI and BamHI sites of plasmid pGH6 (D. V. Goeddel et al., Nature 281, 544 [1979])) to form the plasmid pHS32. Plasmid pHS32 was cleaved with XbaI, phenol extracted, chloroform extracted and ethanol precipitated. It was then treated with 1 μl E. coli polymerase I, Klenow fragment (Boehringer-Mannheim) in 30 μl polymerase buffer (50 mM potassium phosphate pH 7.4, 7 mM MgCl2, 1 mM β-mercapto- ethanol) containing 0.1 mM dTTP and 0.1 mM dCTP for 30 minutes at 0° C. then 2 hr. at 37° C. This treatment causes 2 of the 4 nucleotides complementary to the 5' protruding end of the XbaI cleavage site to be filled in:

Two nucleotides, dC and dT, were incorporated giving an end with two 5' protruding nucleotides. This linear residue of plasmid pHS32 (after phenol and chloroform extraction and recovery in water after ethanol precipitation) was cleaved with EcoRI. The large plasmid Fragment was separated from the smaller EcoRI-XbaI fragment by PAGE and isolated after electroelution. This DNA fragment from pHS32 (0.2 ug), was ligated, under conditions similar to those described above, to the EcoRI-Taq I fragment of the tryptophan operon (0.01 ug). In this process the Taq I protruding end is ligated to the XbaI remaining protruding end even though it is not completely Watson-Crick base-paired:

A portion of this ligation reaction mixture was transformed into E. coli 294 cells as in part I. above, heat treated and plated on LB plates containing ampicillin. Twenty-four colonies were selected, grown in 3 ml LB media, and plasmid isolated. Six of these were found to have the XbaI site regenerated via E. coli catalyzed DNA repair and replication:

```
—TCTAGA—      —TCTAGA—
—AGCTCT—  →   —AGATCT—
```

These plasmids were also found to cleave both with EcoRI and HpaI and to give the expected restriction fragments. One plasmid 14, designated pTrp 14, was used for expression of heterologous polypeptides, as next discussed.

The plasmid pHGH 107 (D. V. Goeddel et al, Nature, 281, 544, 1979) contains a gene for human growth hormone made up of 23 amino acid codons produced from synthetic DNA fragments and 163 amino acid codons obtained from complementary DNA produced via reverse transcription of human growth hormone messenger RNA.

This gene, 3, though it lacks the codons of the "pre" sequence of human growth hormone, does contain an ATG translation initiation codon. The gene was isolated from 10 μg pHGH 107 after treatment with EcoRI followed by E. coli polymerase I Klenow fragment and dTTP and dATP as described above. Following phenol and chloroform extraction and ethanol precipitation the plasmid was treated with BamHI.

The human growth hormone ("HGH") gene-containing fragment 3 was isolated by PAGE followed by electroelution. The resulting DNA fragment also contains the first 350 nucleotides of the tetracycline resistance structural gene, but lacks the tetracyline promoter-operator system so that, when subsequently cloned into an expression plasmid, plasmids containing the insert can be located by the restoration of tetracycline resistance. Because the EcoRI end of the fragment 3 has been filled in by the Klenow polymerase I procedure, the fragment has one blunt and one sticky end, ensuring proper orientation when later inserted into an expression plasmid.

The expression plasmid pTrp14 was next prepared to receive the HGH gene-containing fragment prepared above. Thus, pTrp14 was XbaI digested and the resulting sticky ends filled in with the Klenow polymerase I procedure employing dATP, dTTP, dGTP and dCTP. After phenol and chloroform extraction and ethanol precipitation the resulting DNA was treated with BamHI and the resulting large plasmid fragment isolated by PAGE and electroelution. The pTrp14-derived fragment had one blunt and one sticky end, permitting recombination in proper orientation with the HGH gene containing fragment 3 previously described.

The HGH gene fragment 3 and the pTrp14 Xba-BamHI fragment were combined and ligated together under conditions similar to those described above. The filled in XbaI and EcoRI ends ligated together by blunt end ligation to recreate both the XbaI and the EcoRI site:

HGH gene initiation

This construction also recreates the tetracycline resistance gene. Since the plasmid pHGH 107 expresses tetracycline resistance from a promoter lying upstream from the HGH gene (the lac promoter), this construction, designated pHGH 207, permits expression of the gene for tetracycline resistance under the control of the tryptophan promoter-operator. Thus the ligation mixture was transformed into E. coli 294 and colonies selected on LB plates containing 5 ug/ml tetracycline.

A. Construction of pHGH 107-11

Figure 1:
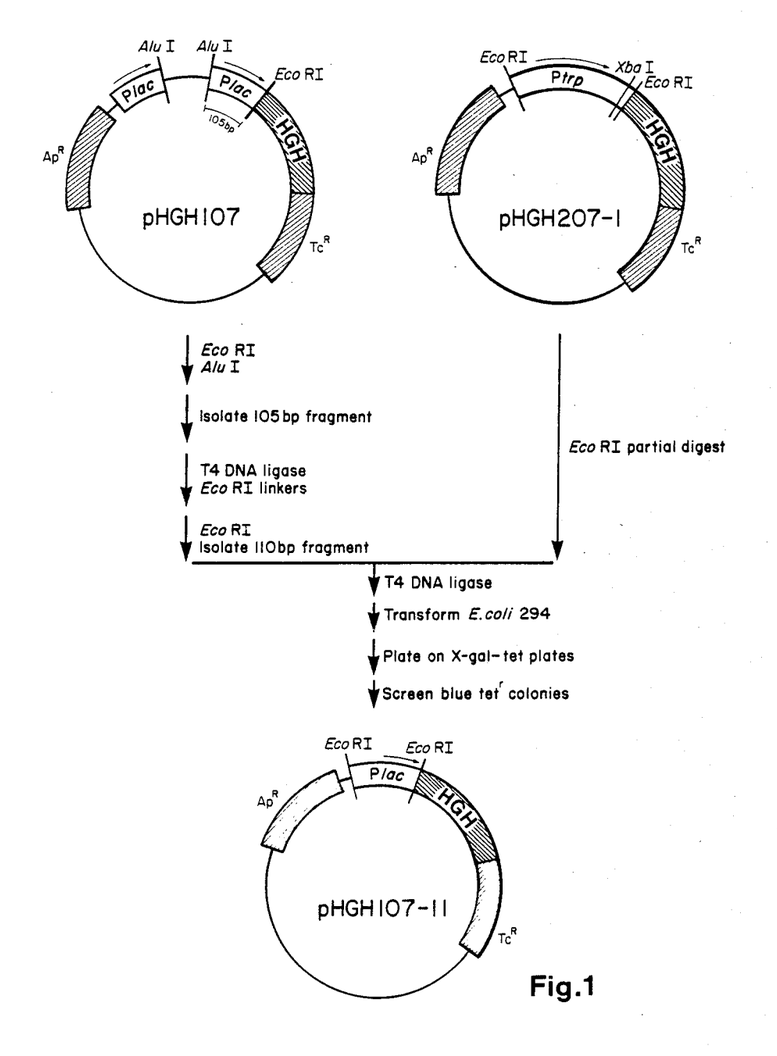
FIG. 1 depicts the construction of plasmid pHGH107-11 which is employed in the construction depicted in FIG. 2.

Plasmid pHGH 107-11 was derived from pHGH 107, a plasmid that has been described previously (Goeddel et al., 1979, Nature 281, 544–548). Both plasmids are derived from pBR322 and have the gene for HGH inserted as described. (See FIG. 1) pHGH 107-11 has a single lac-promoter fused to the HGH-gene whereas pHGH 107 has two lac-promoters separated by a heterologous piece of DNA. To obtain pHGH 107-11 we isolated an EcoRI-AluI 105 bp DNA fragment using 6 percent polyacrylamide gels. To this fragment that has one blunt end we ligated, using T4-polynucleotide ligase, an EcoRI linker with the following sequence:
EcoRI
5'-CGCGAATTCGCG
3'-GCGCTTAAGCGC This ligated material then was treated with EcoRI that cleaves in the middle of the linker and also cleaves concatemers of the DNA fragment covalently linked through the original EcoRI site. The mixture is separated on a 12 percent polyacrylamide gel and a fragment whose size is slightly increased, from 105 bp to 110 bp, is extracted and ethanol precipitated. This fragment now has EcoRI sticky ends on either end and is ready to be inserted in a vector derived from pHGH 207-1.

Plasmid pHGH 207-1, having a single trp-promoter, has obtained by removal of the double lac-promoter from pHGH 207 that has a double lac-promoter followed by a single trp-promoter. This was done as follows: The trp-promoter 310 bp DNA fragment was obtained from pFIF trp 69 (see Goeddel et/al., Nucleic Acids Research, 8, 4057 (1980)) by digestion with EcoRI. This fragment was inserted into pHGH 107 (see FIG. 1), opened with EcoRI, using T4 DNA ligase. Thus, a plasmid was obtained (pHGH 207) that has a double lac promoter followed by the trp-promoter, flanked by EcoRI sites. The thus obtained pHGH 207 was digested with BamHI; this was partially digested with EcoRI and the largest fragment was isolated. This fragment therefore has the entire trp-promoter. From pBR322 the largest EcoRI-BamHI fragment was isolated. Both fragments were ligated and the mixture was used to transform E. coli 294 Tet'. Amp' colonies were isolated and most of them had the plasmid with the stucture as shown for pHGH 207-1.

With the restriction enzyme EcoRI this plasmid (pHGH 207-1) was cleaved and the large fragment, the vector, was isolated from a 6 percent gel. To about 0.1 ug of this vector DNA was added a 5-fold molar excess of the 100 bp EcoRI fragment containing the entire lac-promoter/operator as described above. The fragments were covalently joined using T4 DNA-ligase and the mixture was used to transform *E. coli* 294 according to standard procedures. Cells were plated on X-gal-indicator plates containing 5 ug/ml tetracycline. Blue colonies were picked containing the plasmid structure of pHGH 107-11.

B. Preparation of the Sequence Containing Lac-Pribnow Box and Lac-Operator

About 10 ug pHGH 107-11 was digested with HpaII. A unique 450 bp fragment was isolated. This DNA then was digested with PstI and the resulting 200 bp fragment was isolated (see FIG. 2). This fragment has one sticky HpaII end corresponding to position −19 with respect to the start point of transcription. The lac-Pribnow box is followed downstream by the lac-operator sequence. Nucleotide +1 occurs in the initial part of the lac-operator sequence. This fragment ends with sequences of HGH up to the PstI site (see Goeddel et al. Supra).

C. Preparation of Sequence Containing Trp −35 Consensus Sequence

Figure 2:
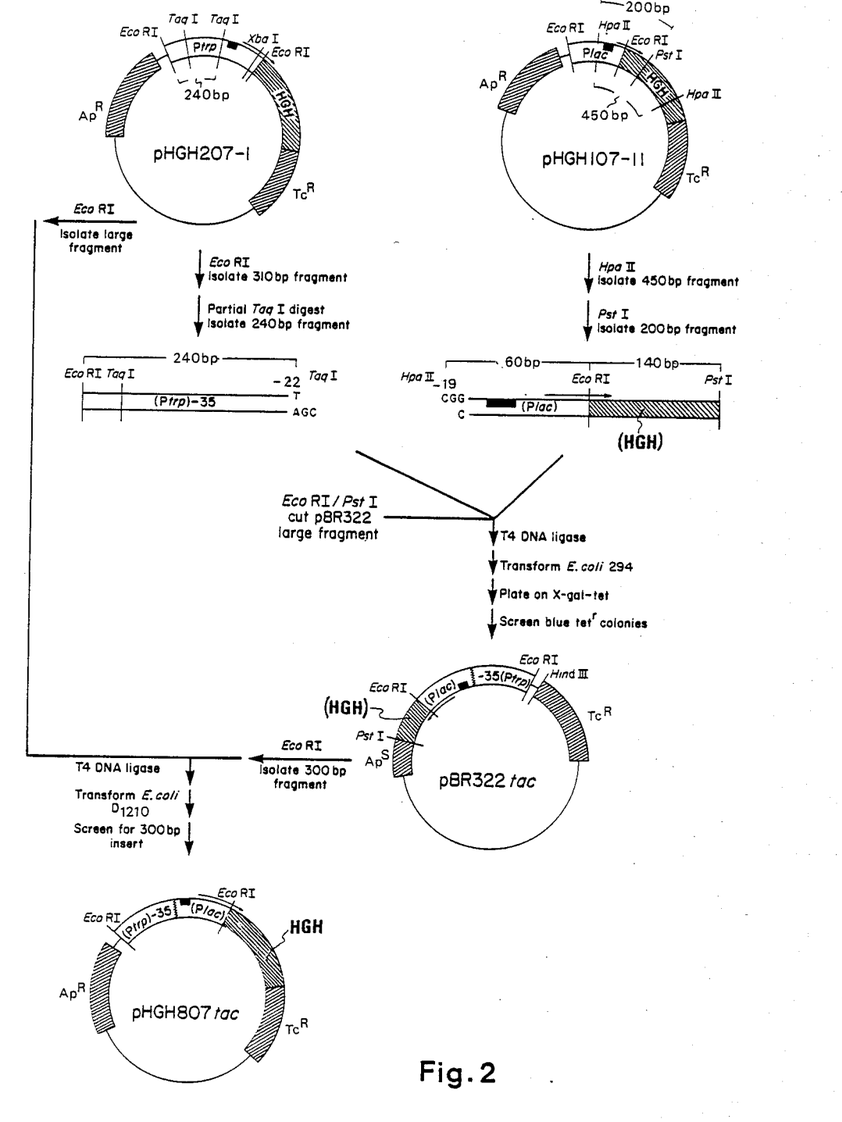
FIG. 2 depicts the origins of DNA fragments, derived respectively from trp and lac promoter harboring plasmids, which were used to construct a plasmid harboring a hybrid promoter/operator hereof operably linked to the structural gene encoding human growth hormone (HGH)—namely, pHGH807-tacI. The hybrid promoter/operator is a fusion of a sequence upstream from position −22 of the trp promoter with a sequence downstream from position −19 of the lac promoter/operator. The black box depicted in the P lac region is the Pribnow box sequence. The fusion point is indicated by the jagged line. The resultant plasmid carries ampicillin and tetracycline resistance genes. The direction of transcription is indicated by the arrow.

The part of the tac-promoter derived from the trp-promoter is obtained as follows: A 310 bp EcoRI fragment was isolated from about 10 ug pHGH 207-1 (prepared as described above). This fragment contains the entire trp-promoter sequences including the trp-repressor binding site but lacks the trp attenuator. This 310 bp fragment was partially digested with TaqI. The 240 bp fragment that contains all the sequences from the upstream EcoRI site to the TaqI site at −22 position, but therefore, lacks the trp-Pribnow box, was isolated from a 6 percent gel. As vector there was used the large EcoRI-PstI fragment derived from pBR322. These three fragments were mixed and ligated, using standard techniques, forming a circle only in one way. After transformation and plating as described above several blue colonies were found to have plasmids pBR322-Ptac13 as shown in FIG. 2.

D. Construction of pHGH 807tacI

Figure 3:
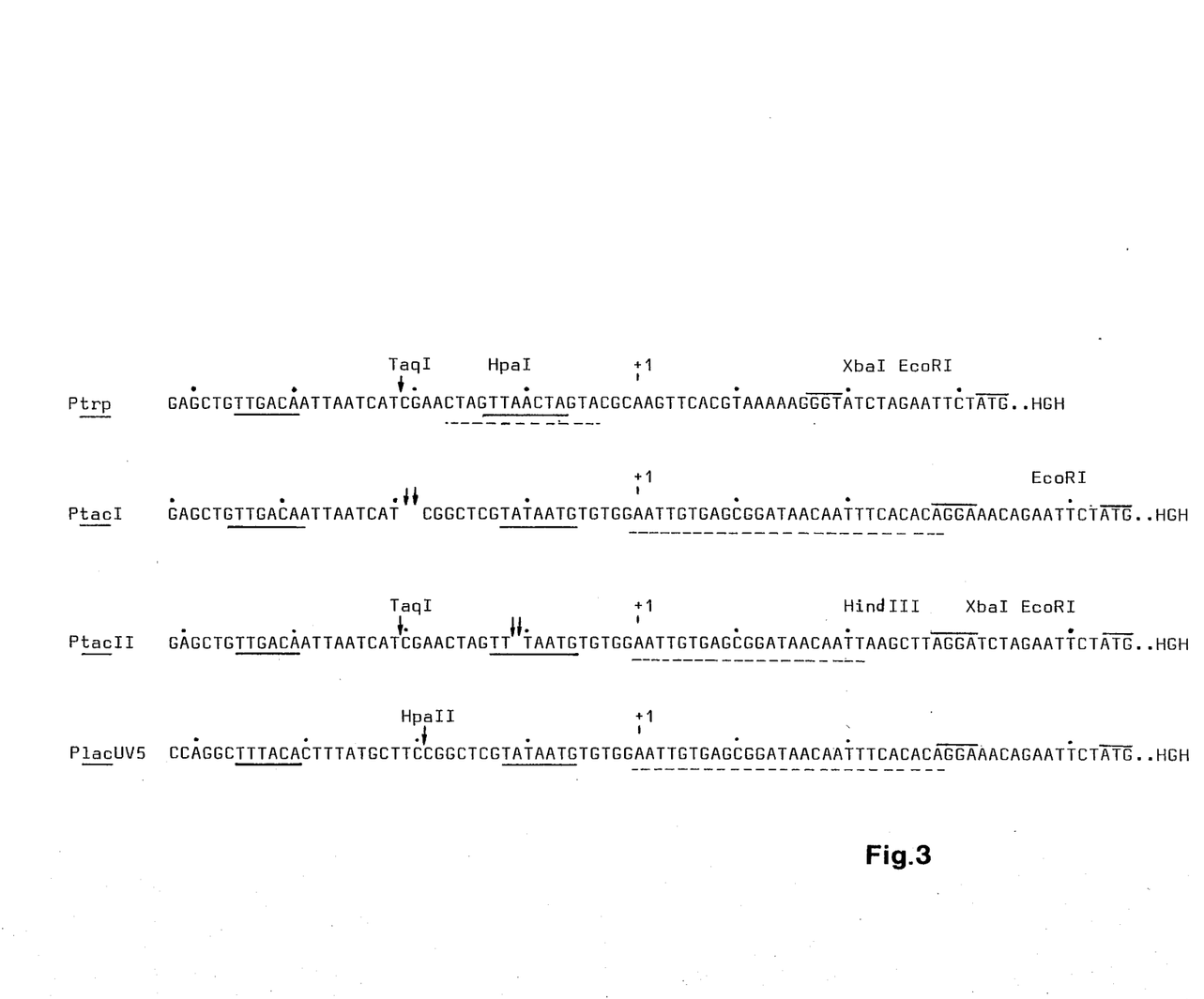
Figure 4:
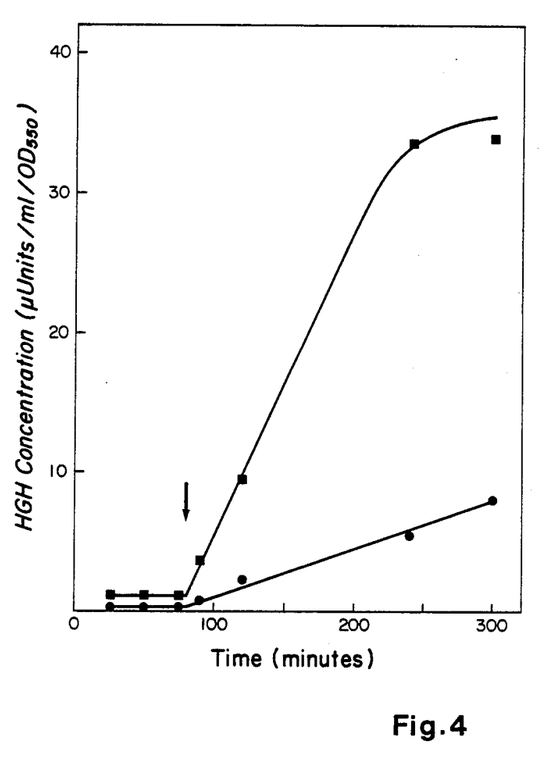

It was anticipated that this promoter might be very powerful and its expression therefore might cause harmful or lethal effects on the cell. By directing transcription towards the destroyed amp gene, as is the case in pBR322tacI, a nonsense protein is formed which is expected to be degraded rapidly, hence is not expected to be lethal. Subsequently, the tac-promoter was excised with EcoRI and the 300 bp fragment was inserted into a vector derived from pHGH 207-1 (from which the trp promoter was removed using EcoRI digest). After ligation, the mixture was used to transform *E. coli* D$_{1210}$ (lac i$^q$). In these cells there is an overproduction of lac-repressor protein; therefore, the tac-promoter having a natural lac-operator sequence is supressed and no lethal accumulation of any gene product occurs. The resulting plasmid is shown in FIG. 2 (pHGH 807tacI). The relevant sequences of Ptrp, Plac and PtacI and PtacII are given in FIG. 3.

E. Construction of the Hybrid rrn-lac and rac 5-16 Promoters

The DNA fragment that codes for one of the 8 tandem ribosomal-RNA promoters (rrn B) of *E. coli* was derived from plasmid pKK3535 which was obtained as follows: As the nucleotide sequence of both the 7.5 kb insert of pKH 2361 and the 4.3 kb plasmid pBR 322 are available (Brosius et/al., *Proceedings of the National Academy of Sciences*, 77, 201, (1980) and *Proceedings of the National Academy of Sciences* 75, 4801 and Sutcliff, (1978) Cold Springs Harbor Symp. Quant. Biol. 43, 77), the 7.5 kb Bam H I fragment from pKK 2361 was subcloned into the Bam H I site of pBR 322. After ligation *E. coli* strain HB1O1 was transformed and ampicillin-resistant, tetracycline-sensitive colonies were screened for plasmids with the predicted size. Three out of twelve transformants were further tested by digestion of their plasmid DNA with Eco RI. In all cases three fragments (6.17 kb, 3.54 kb, and 2.15 kb) were resolved on a 1 percent agarose gel, indicating that the 7.5 kb fragment carrying the rrn B operon was cloned into vector pBR 322 in the same orientation. Cells from one of the three positive colonies were grown and plasmid pKK 3535 was isolated. This plasmid was digested with HindIII and SacII which gave a 906 bp DNA fragment that contains the entire two rrn-B tandem promoters. This fragment has one AluI site and was cut with that enzyme. EcoRI linkers were ligated to this AluI site as described before (See FIG. 1) and this ligation mixture subsequently was digested with HpaII and EcoRI. The unique HpaII site on this fragment is located at position −28 with respect to the transcription initiation site of the first rrn B-promoter. Thus a 130 bp EcoRI-HpaII fragment was obtained.

The lac-part of the hybrid promoter was exactly the same as described before in connection with the construction of the tac-promoter, namely the 200 bp HpaII-Pst fragment. As described, the HpaII end is at position −19 with respect to the transcription initiation site of the lac-promoter. The rrn-promoters are extremely powerful; they are the most efficient promoters of *E. coli* being responsible for the synthesis of large amounts of ribosomal RNA necessary to sustain high growth rates of *E. coli*. Normally this promoter does direct synthesis of an RNA species that is not translated. If this promoter would be forced to synthesize a translatable messenger RNA it would kill the cell. Therefore, during construction of the hybrid rrn-lac promoter, it was important to keep this promoter in a repressed state while under construction.

The 130 bp EcoRI HpaII "Prrn" fragment and the 200 bp HpaII-Pst-"Plac" fragment were ligated with the large EcoRI-Pst fragment of pBR322 exactly as described for the tac-promoter. The resulting plasmid pBR322-Prrnlac is shown (See FIG. 5).

Figure 5:
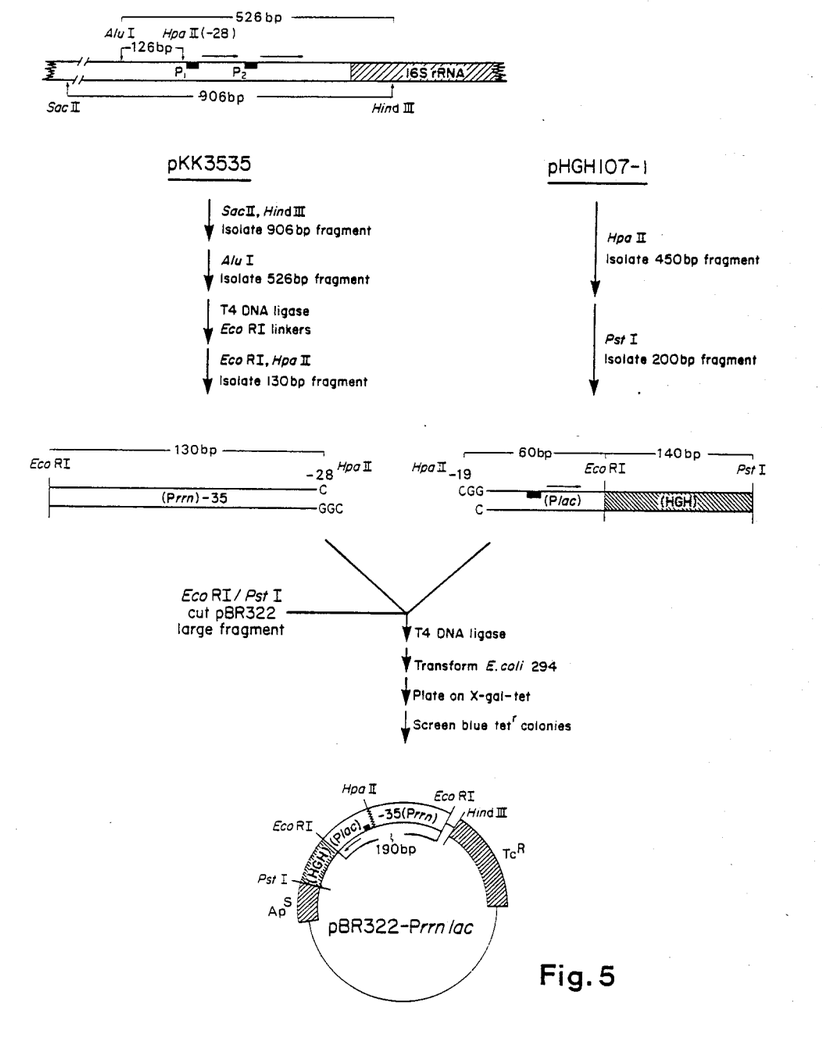
FIGS. 5 and 6 depict the construction of expression plasmid pHGH-Prac5-16, obtained from pHGH-Prrnlac, which harbors a hybrid promoter/operator hereof: a sequence upstream from position −28 of the rrn promoter and a sequence downstream from position −19 of the lac promoter/operator, fused via a synthetically derived DNA sequence.

In the case of the rrn-lac hybrid there is a junction of the position −19 of Plac to nucleotide −28 of Prrn. The distance between the Pribnow box and the −35 area is much too short and no transcription can start at such a promoter. Large amounts of the two promoter fragments in pBR322-Prrnlac were thus obtained. Plasmid DNA (20 ug) was digested with EcoRI and a 190 bp fragment was purified and subsequently digested with HpaII. Both fragments, the 130 bp "Prrn" and the 60 bp "Plac" piece, were purified. To the 130 bp fragment two self-complementary synthetic fragments 1 and 2 were ligated. Their sequence is:

|   | HpaII | SacI | Xho |
|---|---|---|---|
| 1: | CGGAGCTC | | |
| 2: | | CTCGAGAGCT | |

After ligation and digestion with EcoRI and XhoI a DNA fragment of about 140 bp was isolated.

In a similar fashion the 60 bp "Plac" fragment was provided, having two self-complementary synthetic fragments 3 and 4, as follows:

|  | Xho | Xba | ClaI |
|---|---|---|---|
| 3: | TCGAGTCTAGAAT | | |
| 4: | | CAGATCTTAGC | |

Figure 6:
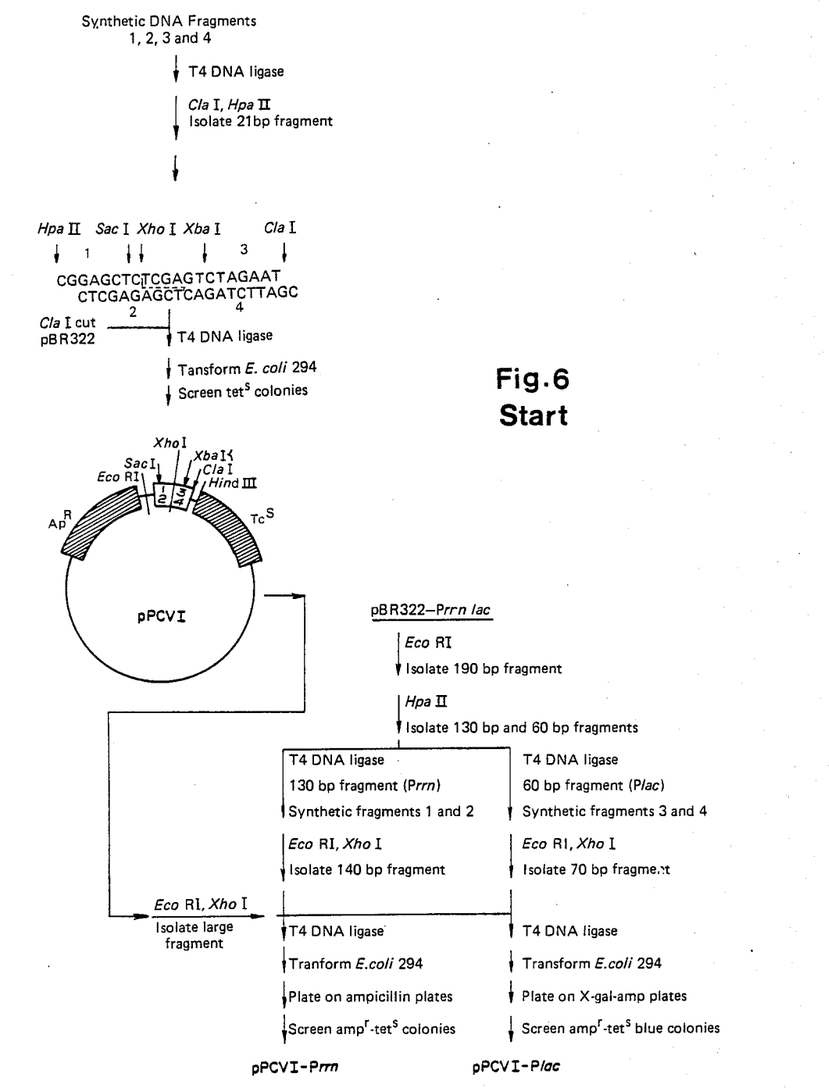

After digestion of the ligation mixture with EcoRI and XhoI, a 70 bp fragment was isolated. These two fragments that have a synthetic linker joined to their HpaII end and now have XhoI and EcoRI sticky ends were inserted into vector PCVI that was opened with EcoRI and XhoI. The construction of vector PCV I is as follows (see FIG. 6):

F. Construction of PCV I

The four fragments, PP-1 through PP-4, were synthesized according to the method of Cren et/al., *Nucleic Acids Research*, 8, 2331 (1980). The synthesis of the fragments were accomplished from the appropriate solid supports by sequential addition of the appropriate fully protected mono- or trimer-blocks. The cycles were carried out under the same conditions as described in the synthesis of oligothymic dilic acid (see Crea et/al., Supra.). The final polymer was treated with base (conc. aq. $NH_3$) and acid (80 percent aq. AcOH), the polymer pelleted off and the supernatant evaporated to dryness. The residue, dissolved in 4 percent ag. $NH_3$, was washed with ether and used for the isolation of the fully deprotected fragment. Purification was accomplished on h.p.l.c. on Permaphase AAX. Gel electrophoretic analysis showed that each of the fragments, PP-1 through PP-4, had the correct size:

| fragment | sequence | size |
|---|---|---|
| PP-1: | 5¹-CGG.AGC.T.C-3¹ | (8-mer) |
| PP-2: | 5¹-TCG.AGA.GCT.C-3¹ | (10-mer) |
| PP-3: | 5¹-TCG.AGT.CTA.GAA.T-3¹ | (13-mer) |
| PP-4: | 5¹-CGA.TTC.TAG.A.C-3¹ | (11-mer) |

The synthetic self-complementary sequences 1, 2, 3, and 4, were mixed and ligated. The mixture was cleaved with HpaII and ClaI and the 21 bp fragment was purified and inserted into ClaI opened pBR322. Since the ClaI site of pBR322 is within the tet-promoter hosts containing an insert could be recognized easily since they are tet-sensitive. Therefore, after transformation the cells were plated on amp-plates. Colonies were transferred on tet-plates and the plasmid DNA was analyzed of those that are tet-sensitive. The resulting plasmid is shown and is called PCV I (Promoter Cloning Vector I). This vector has six unique restriction sites in front of the tet gene. A promoter inserted into any of these sites will restore useful tet-resistance.

G. Insertion of the 140 bp "Prrn" and 70 bp "Plac" Sequences into PCV I

Plasmid PCV I was opened with XhoI and EcoRI and the large vector fragment was isolated. Using standard techniques, the fragments aforementioned were inserted. Since only plasmids that have an insert can re-close, the majority of the plasmids had the structure as shown (PCV I-Prrn and PCV I-Plac). The plasmid was amplified and isolated and the two fragments of 140 bp and 70 bp isolated. They were mixed, ligated and the concatemers cleaved with EcoRI and XhoI. The digest was separated on a 6 percent gel and a 210 bp fragment recovered. This fragment was inserted into a vector derived from pHGH 207-1 (of which the trp-promoter was removed with EcoRI; see above).

```
Prrn Lac        -35        -28 SacI XhoI XbaI
                    (1)       ↓↓       ↓   (3)
---TTTTAAATTTCCTCTTGTCAGGCCGGAGCTCTCGAGTCTAGAAT---
---AAAATTTAAAGGAGAACAGTCCGGCCTCGAGAGCTCAGATCTTAGC---
                             (2)              (4)
     (Prrn)              synthetic insert -19   -10
     CGGCTCGTATAATGTGTGGA   lac-operator HGH
     CGAGCATATTACACACCT
        (Plac)
```

Thus constructed is a hybrid promoter having a 21 bp insert in the $-28/-19$ junction. The distance between the Pribnow box and $-35$ sequence is too long to be active. To activate this promoter, that is to establish the proper distance between the Pribnow box and the $-35$ sequence, the plasmid pHGH-Prrnlac was cleaved with SacI and XbaI. The sticky ends were removed with enzyme S1 and the blunt ends were ligated. The sequence of the resulting "rac"-promoter, see pHGH-Prrnlac (see FIG. 6), is shown below, together with the lac and the rrn B promoter:

```
Plac/UV5 CCAGGCTTTACACTTTATGCTTCCGGCTCGTATAATGT—
                                              +1
                           GTGGAATTGTGAGCGGATAACAATTTCACACAGGAAACAGAATTCTATG
Prac 5-16 TTCCTCTTGTCAGGCCGGAAT CGGCTCGTATAATGT—
                                              +1
                           GTGGAATTGTGAGCGGATAACAATTTCACACAGGAAACAGAATTCTATG
                                              +1
PrrnB    TTCCTCTTGTCAGGCCGGAAT AACTCCCTATAATGCGCCACCACTG
```

H. Construction of TacII Hybrid Promoter

Figure 7:
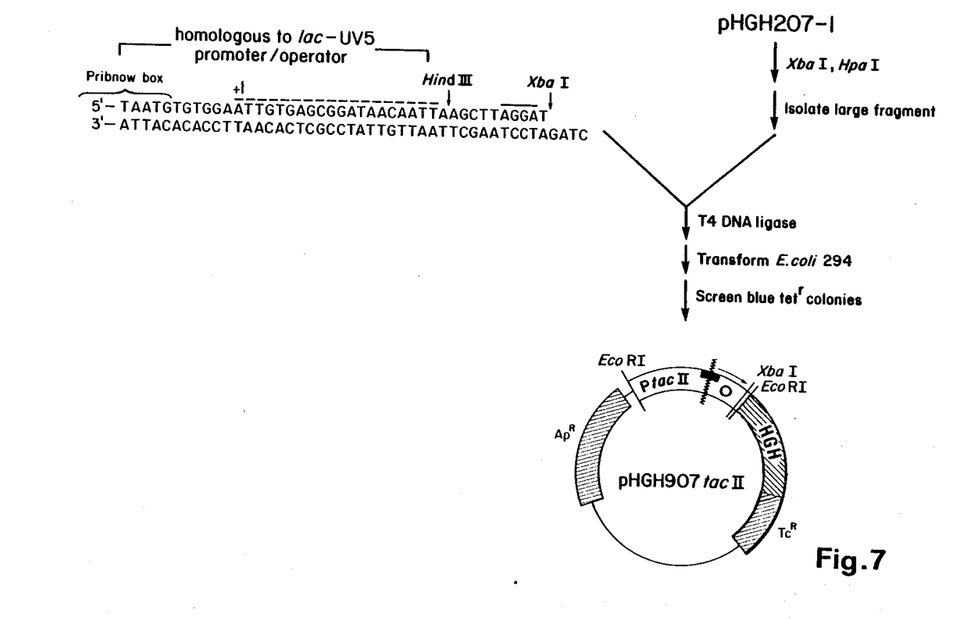
FIG. 7 depicts the construction of plasmid pHGH907tacII which harbors a hybrid promoter/operator hereof: a sequence downstream from position −10 of the lac promoter operator and a sequence upstream from position −12 of the trp promoter/operator. This plasmid also contains a portable Shine-Dalgarno sequence.
Figure 8:
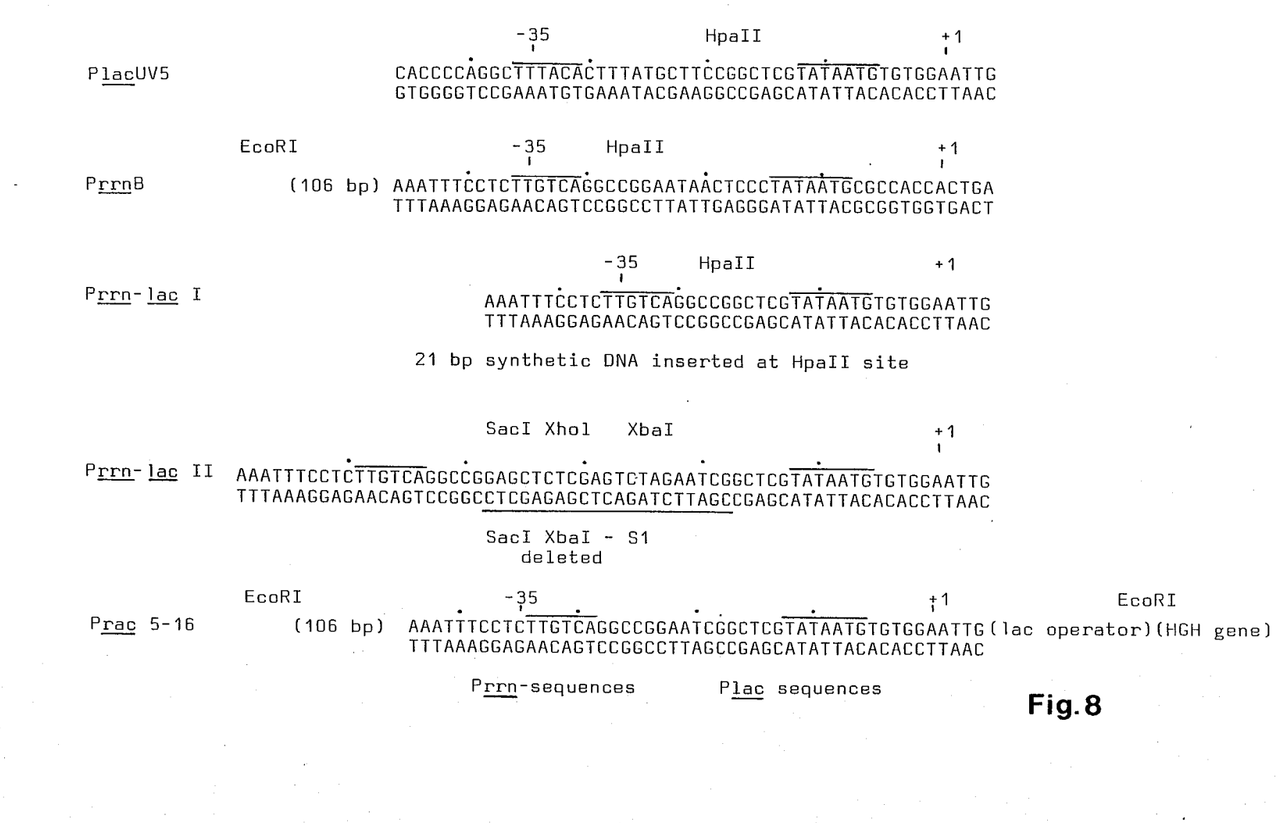
FIG. 8 depicts the DNA sequences of the Lac-UV5, the rrnB, the shortened (Prrn-lacI), the lengthened (Prrn-lacII) and the activated (rac5-16) hybrid promoters. The respective −35 sequence and the Pribnow box sequence are overlined. The synthetic insert of Prrn-lacII is underlined. The transcription start site of Plac and Prrn or the nucleotide corresponding to that start site in the case of the Prrn-lacI, the Prrn-lacII and the Prac5-16 is indicated.

Another hybrid promoter was constructed which is controlled by the lac-repressor and which is not affected by the trp-repressor. In the trp-promoter the trp-repressor binding site overlaps with the Pribnow box (Siebenlist, Supra.) which in this case also specifies a HpaI site (gTTAAC). (see FIG. 7). Sequences downstream from this HpaI site were replaced by a synthetic DNA fragment. Thus, the trp-repressor binding site was destroyed. Plasmid pHGH207-1 was opened with HpaI and XbaI and a synthetic DNA fragment of 42 bp was inserted. The sequence of this synthetic fragment is identical to that found in the homologous area of the lac-UV5 promoter/operator. Thus the first 2 bp of the trp-Pribnow box (TTAACTA) are joined to the last 5 bp of the lac-UV5 Pribnow box (TATAATG) resulting in a hybrid Pribnow box (TTTAATG). Downstream of this hybrid Pribnow box is a 5 basepair sequence which is identical to that found in the lac-UV5 promoter/operator. This 5 bp sequence is the left arm of the region of symmetry that flanks the core of the natural lac-operator. This 5 bp sequence is followed by nucleotides that specify the core of the lac-operator. (Heyneker et al., Nature 263, 748 (1976)). The lac-operator is followed by a HindIII site and a Shine-Dalgano sequence which has a 4 basepair homology with 16s ribosomal RNA. The synthetic fragment ends with an XbaI site by which it is fused to the HGH gene. Thus, the Shine-Dalgarno area is flanked by two different restriction sites which are unique on the plasmid. It should be noted that the tacII promoter/operator lacks the right arm of the region of symmetry that flanks the natural lac-operator. The resultant hybrid promoter, pHGH907tacII thus contains an operator corresponding to the lac promoter and, joined within the respective Pribnow Box regions, the 5'-DNA sequence upstream of the trp promoter.

I claim:

1. A hybrid promoter/operator capable of directing E.coli DNA-dependent RNA polymerase transcription of a recombinant DNA fragment positioned downstream therefrom comprising:
   (a) a portion of a promoter/operator sequence which portion is capable of being derepressed by induction and which promoter exhibits a first strength, and,
   (b) operably positioned upstream therefrom, a fragment comprising the −35 consensus sequence and 5' flanking region of a second promoter having a greater strength;
   elements (a) and (b) being covalently linked between about said −35 consensus sequence and the Pribnow box of said promoter/operator sequence.

2. A hybrid promoter/operator according to claim 1 wherein said elements (a) and (b) are linked at a position between about nucleotide base pairs −10 to −35.

3. A hybrid promoter/operator according to claim 1 wherein said elements (a) and (b) are linked via complementary restriction sites thereon.

4. A hybrid promoter/operator according to claim 3 wherein said complementary restriction sites are synthetically derived.

5. A hybrid promoter/operator according to claims 1, 2, 3, or 4 wherein said element (a) is derived from a promoter operator selected from the group consisting of lac, gal P2, ara BAD, ara C and gal P1.

6. A hybrid promoter/operator according to claims 1, 2, 3, or 4 wherein said element (b) is derived from a promoter selected from the group consisting of trp, rrn, lambda PR, lambda PL, str, spc and rpoB.

7. An E. coli culture capable of producing a heterologous polypeptide by expression of a gene coding therefor, said expression being directed by a hybrid promoter/operator according to claim 1.

8. A hybrid promoter/operator which comprises:
   (a) an operator DNA sequence of a first promoter/operator which is capable of being derepressed by induction, and which comprises that sequence immediately downstream of a position between about −10 and −35 of said first promoter operator; and
   (b) upstream from the sequence of (a), a DNA sequence which comprises that sequence of a second promoter which is immediately upstream of a position between about −10 and −35 of said second promoter.

9. A hybrid promoter/operator capable of directing E.coli DNA-dependent RNA polymerase catalyzed transcription which comprises:
   (a) an upstream portion comprising the DNA sequence of a first promoter, which sequence is upstream of a position between about −10 and −35 of such first promoter; and
   (b) a downstream portion comprising the DNA sequence of a second promoter/operator which sequence is downstream of a position between about −10 and −35 of said second promter/operator, and which sequence contains an operator which is capable of being derepressed by induction.

10. The hybrid promoter/operator of claims 1, 8, or 9 wherein the operator sequence is the operator sequence of the lac promoter/operator.

11. The hybrid promoter/operator of claim 10 which comprises the DNA sequence downstream from position −19 of the lac promoter/operator linked to, and downstream from, the DNA sequence upstream of position −22 of the trp promoter.

12. A hybrid promoter/operator according to claim 10 comprising a DNA sequence upstream from position −12 of the trp promoter linked to a DNA sequence which comprises the core of the lac operator.

13. The hybrid promoter/operator of claim 10 which comprises a DNA sequence downstream from position −19 of the lac promoter operator linked downstream from, and via a synthetic DNA sequence to, a DNA sequence upstream from position −28 of the rrn promoter.

14. A replicable expression vehicle comprising a heterologous gene insert, the expression of which is under the control of the hybrid promoter/operator of claims 1, 8, or 9.

15. An E.coli strain transformed with the vehicle according to claim 14.

* * * * *